(12) United States Patent
Tuunanen

(10) Patent No.: US 6,596,162 B2
(45) Date of Patent: Jul. 22, 2003

(54) VESSEL AND ROD

(75) Inventor: Jukka Tuunanen, Helsinki (FI)

(73) Assignee: Thermo Labsystems Oy, Helsinki (FI)

( * ) Notice: Subject to any disclaimer, the term of this patent is extended or adjusted under 35 U.S.C. 154(b) by 50 days.

(21) Appl. No.: 09/808,232

(22) Filed: Mar. 14, 2001

(65) Prior Publication Data

US 2001/0022948 A1 Sep. 20, 2001

(30) Foreign Application Priority Data

Mar. 14, 2000 (FI) ............................................. 20000583

(51) Int. Cl.[7] .............................. B03C 1/00; B03C 1/28; B01L 3/02
(52) U.S. Cl. ....................... 210/222; 436/526; 422/100; 422/101; 422/102
(58) Field of Search ................................. 210/222, 695; 436/526; 422/100, 101, 102

(56) References Cited

U.S. PATENT DOCUMENTS 4,649,116 A * 3/1987 Daty et al. ................... 210/222

FOREIGN PATENT DOCUMENTS

| EP | 0 140 787 | 5/1985 |
|---|---|---|
| WO | WO 87/05536 | 9/1987 |
| WO | WO 94/18564 | 8/1994 |
| WO | WO 94/18565 | 8/1994 |
| WO | WO 96/12958 | 5/1996 |
| WO | WO 96/12959 | 5/1996 |
| WO | WO 99/04239 | 1/1999 |
| WO | WO 99/40444 | 8/1999 |

OTHER PUBLICATIONS

European Search Report; EP 02017578.2; The Hague; L. Decanniere; Oct. 24, 2002.
Correspondence in Corresponding Finland Appl. No. 20000583 (dated Feb. 28, 2001).
"Thermo Labsystems Kingfisher™ Magnetic Particle Processor"; Labsystems Oy. Undated.
International Search Report; PCT/FI01/00242; Jul. 4, 2001; Ulf Nystrom/ELY.

* cited by examiner

*Primary Examiner*—David A. Reifsnyder
(74) *Attorney, Agent, or Firm*—Fish & Richardson P.C.

(57) ABSTRACT

The invention relates to a vessel and to a rod used with the vessel for collecting magnetic particles from a liquid containing the particles in the vessel, or for releasing the particles into a liquid in the vessel. The minimum distance from the rod, when inserted into the vessel, from the inner wall surface of the vessel is great enough at each point to resist or prevent any liquid ring or ring part from being formed between the vessel and the rod, which ring could be removed along with the rod. In this manner, liquid is prevented from being removed from the vessel along with the rod.

28 Claims, 3 Drawing Sheets

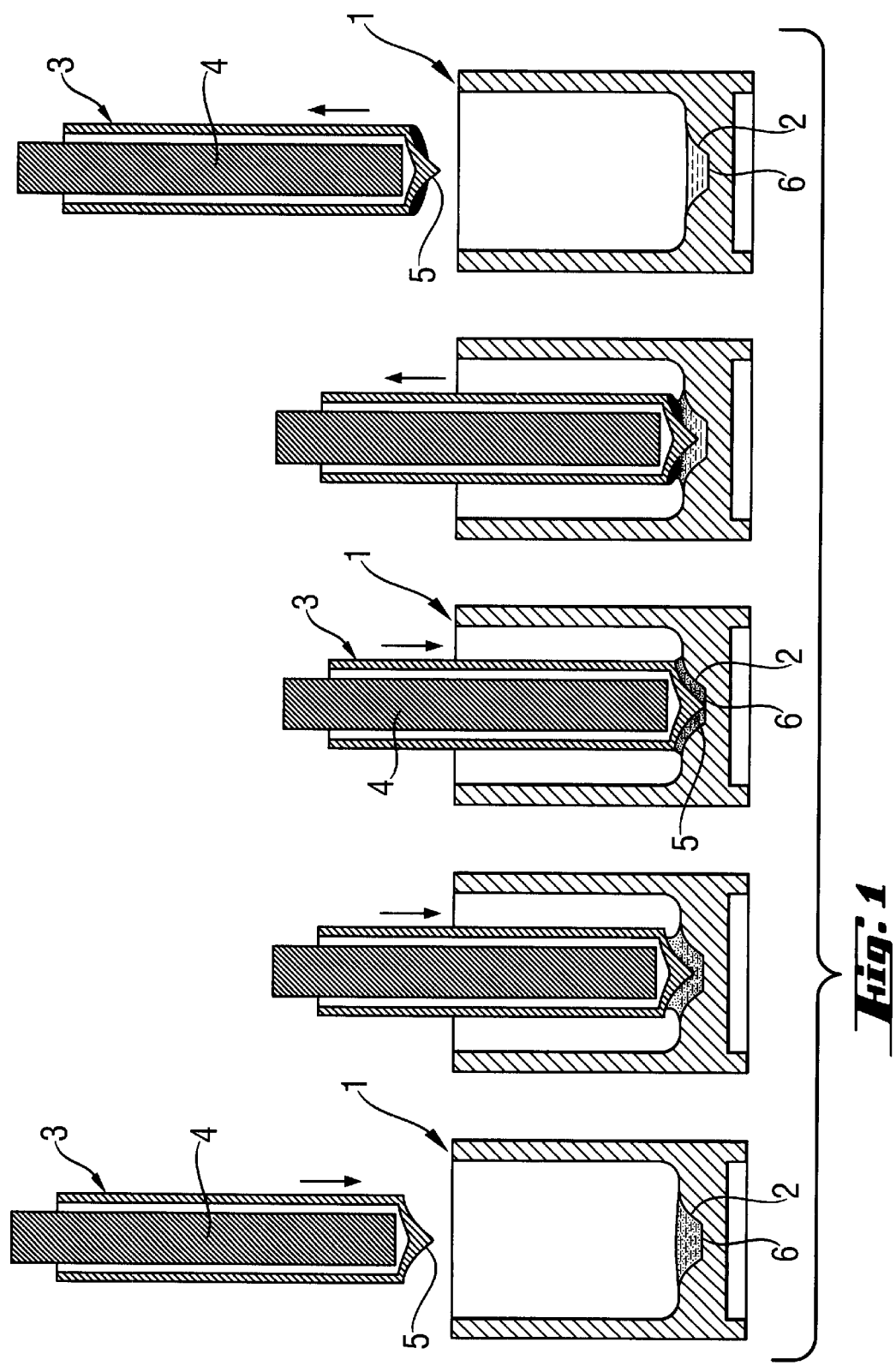

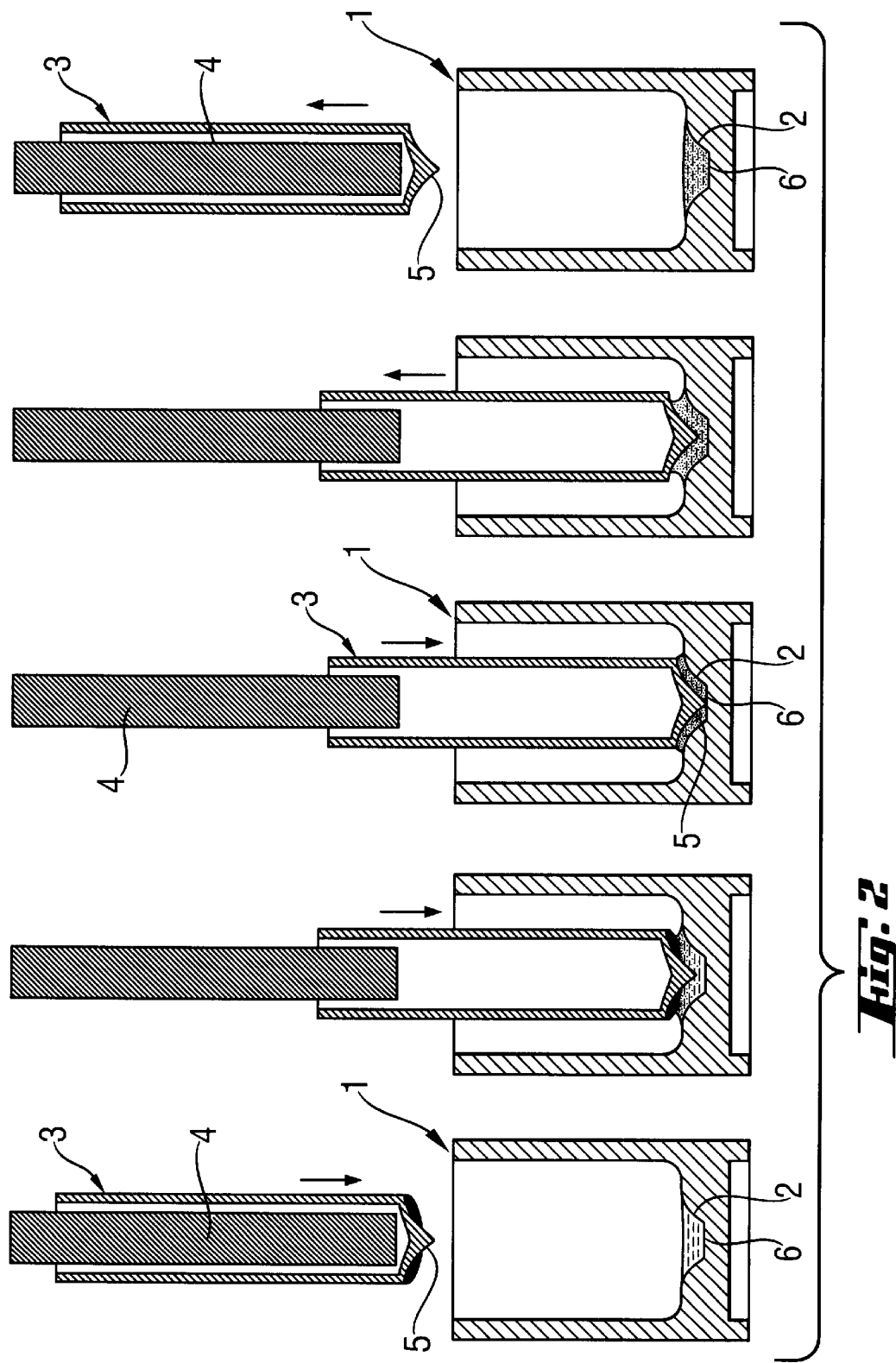

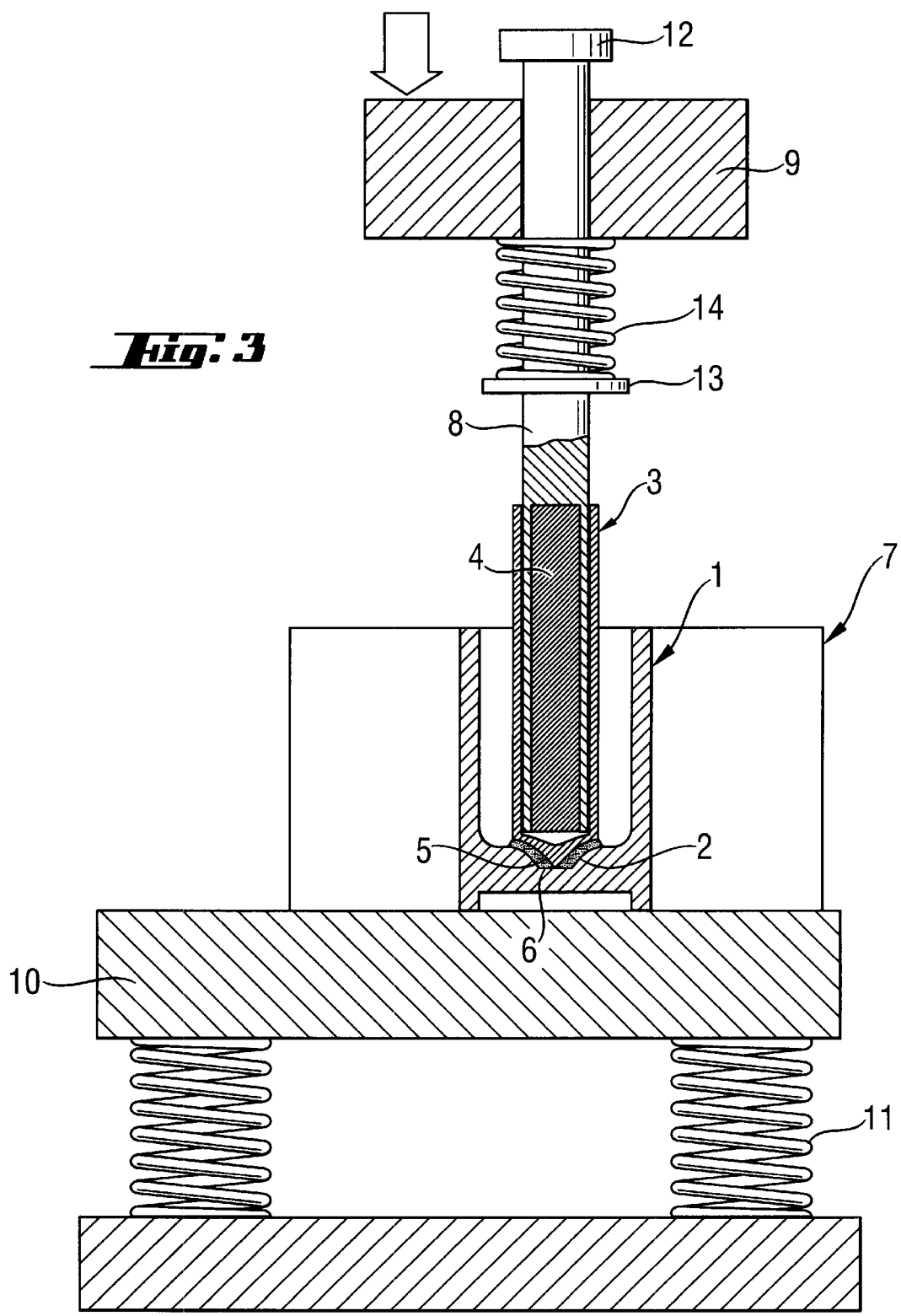

VESSEL AND ROD

FIELD OF TECHNOLOGY

The invention relates to the processing of compositions containing magnetic particles, in which the particles are collected from a vessel containing the composition or are released as a composition in the vessel, and in which a magnetic rod is used to collect the particles to its tip or to release them from its tip. The invention relates specifically to the vessel and the rod used in the processing. The invention can be used for instance in various manufacturing, purification or analysis methods.

TECHNOLOGICAL BACKGROUND

Magnetic particles are used in various chemical processes as a solid phase, to whose surface a given component adheres. Owing to the particles, the available surface of the solid phase becomes as large as possible. The particle size is typically in the range from 0.05 to 10 µm. The particles can be moved by means of a magnetic field. Thus, for instance in a solution they may be transferred to the wall of a vessel, so that the remaining solution can be removed from the vessel by decanting or pipetting. The particles can also be separated from the solution by immersing a magnetic rod in the solution. Magnetic rods are also known, which comprise a vertically moving magnet within a cover. With the magnet in lower position, the particles can be collected on the rod surface, especially at its end. When the magnet is raised into upper position, the particles can be released from the rod accordingly.

WO 94/18565 discloses rods used for collecting and transferring magnetic particles. They are preferably equipped with a cover with a sharp tip enclosing a movable magnet. The vessel used jointly with the rod may have a bottom matching the shape of the rod tip. The interstice between the rod and the vessel wall is made narrow on purpose, in order to make the liquid flow as rapidly as possible between the rod and the vessel wall when the rod is moved vertically. This enhances mixing and mass transfer.

GENERAL DESCRIPTION OF THE INVENTION

A vessel for a composition containing magnetic particles and a rod for collecting or transferring particles to be used together with the vessel have now been invented.

The vessel is preferably symmetrical, such as circular, in cross-section, and the cross-sectional shape of the rod matches the cross-sectional shape of the vessel. The rod is equipped with a magnet, by means of which particles are collected on the rod surface, preferably at its tip portion. The magnet is preferably such a magnet whose action can be eliminated, so that the particles can be released from the rod surface.

The magnet is preferably a permanent magnet, and most preferably a magnet that can be shifted between a collecting position and a releasing position within the rod. The direction of movement is especially the longitudinal direction of the rod. The collecting position of the magnet is preferably its lower position, from where it can be raised to the releasing position. The magnet preferably has a length that is significantly greater than its width. This allows particles to be efficiently collected on the rod tip. For the same reason, the upper end of the magnet preferably remains continuously above the composition surface while the particles are collected (cf. WO 96/12958). To this end, the length of the magnet can be clearly greater than the height of the liquid column to be treated. In the magnet, the ratio of its length to its width is preferably at least about 5:1 and most preferably at least about 10:1. The rod preferably slopes downwards at every point, ending in a sharp tip. In this manner, the rod, when lifted from the liquid, tends to retain as small an amount of liquid as possible (cf. WO 94/18565 and WO 94/18564). The use of a long magnet allows more efficient operation in small volumes. A long magnet is useful also in large volumes, because it enlarges the dynamic area at both ends. The tip preferably also has a tapered concave tip portion, so that particles are efficiently released from the rod tip into a small vessel of the same order of magnitude as the tip portion of the rod (cf. WO 96/12959). For the magnetic field to be aligned with this tip portion as efficiently as possible, the height of the tip portion is relatively small compared to the diameter of the magnet. Typically, the ratio of the height of the tip portion to the diameter of the magnet is 1:1–1:2, such as about 1:1.5. The flat shape of the tip also has the purpose of achieving a reliable operating volume that is as small as possible.

Particles can be collected with a specific apparatus, in which the vessels can be placed and which comprises means for moving the rods (cf. WO 94/18565).

Usually a plurality of vessels has been joined to form a plate, especially a matrix-shaped plate, which comprises several rows of vessels in succession. A commonly used plate is the one called micro-titration plate, comprising 8*12 vessels, or wells, at 9 mm intervals. A plate with corresponding outer dimensions and 16*24 wells is also used. The apparatus intended for the treatment of the plates may comprise a row of rods equal to the number of wells in one row (cf. WO 94/18565 and Thermo Labsystems Kingfisher™ Magnetic Particle Processor). The apparatus also allows the operation of several, such as two, plates simultaneously, especially in parallel.

According to a first feature of the invention, the interstice between the vessel and the rod is large enough to prevent the formation of a liquid ring or a ring part rising along with the rod and thereby removing liquid from the vessel. In other words, the liquid flows down between the rod and the vessel under the force of gravity. Ascending water could flow over the edge of the vessel e.g. into an adjacent vessel or in the tip of a removed tip to the subsequent process step. A suitable interstice between the rod and the vessel can be at least about 1 mm, such as at least about 1.5 mm, and preferably at least about 2 mm. In common cases, an interstice above 3 mm does not gain any additional benefit in this respect.

According to a second feature of the invention, the vessel bottom comprises a positioning recess, into which the rod tip is fitted with the rod at a sufficient distance from the inner wall of the vessel at every point. The positioning recess serves to compensate for positioning errors caused by the horizontal movement of the rod and the vessel. The recess centre preferably comprises a horizontal area, whose width corresponds to the positioning margin. The recess shape is preferably identical to that of the tip portion of the rod, so that the interstice between the recess and the tip portion becomes as small as possible. The interstice is preferably 0.05–0.3 mm at the most, such as 0.1–0.2 mm. When a symmetrical vessel and rod are used, the recess will be located at the centre of the vessel. The horizontal area typically has a width in the range 0.5–2 mm, such as about 1 mm. However, the rod is most preferably such that it is usable also in conventional vessels with a flat or concave bottom of various sizes.

According to a third feature of the invention, the apparatus in which the vessel is treated by means of the rod, comprises a vertically elastic means, which yields as the rod is lowered against the vessel bottom. This allows compensation for the positioning error caused by the positioning tolerances of the vertical movement and by the manufacturing tolerances of the rod and the vessel. The elastic means, such as spring means, may be provided in a base included in the apparatus for the vessel, in the rod or its actuating gear, or in a plate comprising several vessels.

The invention is suitable for use especially during operations in very small volumes. The lower limit may be e.g. 10 $\mu$l or even 5 $\mu$l. The invention is suitable for use also when particles are collected from a relatively great volume, e.g. a bacterial culture, and are transferred into a volume that may be up to many times smaller.

DRAWINGS

The accompanying drawings pertain to the detailed description below of some embodiments of the invention.

FIG. 1 shows the steps of collecting magnetic particles with the rod from a small amount of liquid in the vessel according to one embodiment of the invention.

FIG. 2 shows the steps of releasing the magnetic particles adhered to the rod of FIG. 1 into a small liquid amount in the vessel of FIG. 1.

FIG. 3 shows an apparatus of the invention provided with spring means.

DETAILED DESCRIPTION OF SOME EMBODIMENTS OF THE INVENTION

The circular well 1 shown in FIGS. 1 and 2 comprises, at its bottom centre, a bottom recess 2 with relatively steep edges. There is liquid in the well recess.

Together with the well 1, a rod 3 is used, which has a circular cross-section and a diameter considerably smaller than the diameter of the well, but yet greater than the diameter of the recess. The rod has an internal bore starting from the upper end, and an elongated permanent magnet 4 which can be moved within the bore. When the magnet is in the lower position within the rod, magnetic particles can be collected on the rod tip (FIG. 1). The tip portion 5 of the rod tapers in order to be accommodated in the bottom recess 2 of the well.

Magnetic particles adhering to the rod 3 can be released into the liquid in the well 1 (FIG. 2). To this effect, the rod is introduced into the well with the magnet 4 in lower position, then the magnet is removed, and thereafter the rod without the magnet, so that the particles remain in the liquid in the well. Correspondingly, if there are particles in the liquid contained in the well, with the magnet in lower position, the particles are collected from the liquid onto the rod tip. When the rod and the magnet are removed together, the particles are removed along with them.

The tip portion 5 of the rod 3 is concave and ends in a sharp tip. Thus, when particles are detached, they are swept off into the recess 2 as completely as possible, and when the rod is lifted from the liquid, it tends to retain liquid in as small an amount as possible. When particles are collected, they adhere to the concave portion of the tip, encircling it as an annular mass. The recess wall has a matching convex shape, so that the interstice between the rod tip portion and the well is as small as possible. When the rod tip bears against the recess bottom, the liquid automatically finds its way into this interstice owing to adhesion and surface tension. The liquid thus moistens the entire tip portion, where particles may be present as they are being brought into the well with the rod. The liquid remains solidly in the interstice with the rod fitted in position in the recess. When the rod is lifted from the recess, the liquid plate surrounding the tip portion will efficiently sweep the particles along from the top to the bottom by hydrodynamic forces.

When the interstice between the rod 3 and the wall of the well 1 is large enough, no liquid ring or part of it rising along with the rod will be formed in this gap. A suitable interstice is about 1 mm. In the practice, an interstice above approx. 3 mm does not gain any additional benefit in this respect. To break a rising liquid ring that may have arisen in exceptional cases, the mouth portion of the well can be further enlarged (cf. WO 94/18565 FIG. 5). The high lateral walls of the well prevent the liquid from sloshing over to the outside. In this manner, whenever necessary, liquid amounts many times greater than the volume of the bottom recess 2 can be used in the same well.

The bottom of the well 1 has a shape such that a small liquid amount dosed into the well naturally finds its way into the bottom recess 2 as completely as possible. In the recess, the free surface of the liquid will be at a minimum, so that the liquid tends to remain here under the action of surface tension. For the liquid not to remain in the corner between the well bottom and the outer wall, this corner has been given a mildly curved shape. An appropriate radius of curvature of the corner is e.g. 0.5–2 mm, such as about 1 mm.

The bottom of the well 1 is continuously sloping from the corners to the bottom recess 2. Thus the liquid will flow naturally into the bottom recess.

The bottom of the bottom recess 2 in the well 1 comprises a central horizontal area 6. The width of the area is determined by the positioning tolerances, so that it is ensured that the tip of the rod 3 always hits this horizontal area. There will be positioning errors if the wells or the rods are moved horizontally. The width of the horizontal area is then (at least) twice the estimated positioning error. The appropriate width of the area is typically 0.5–2 mm, such as about 1 mm. For the same reason, the interstice between the tip portion 5 of the rod and the wall of the bottom recess is slightly larger at the bottom end than at the top end. The aim is to reduce the interstice to a minimum. It is typically 0.1–0.2 mm.

The ratio of the length to the diameter of the magnet 4 is about 13:1. Owing to the long magnet, the particles are collected as completely as possible precisely to the tip area of the rod 3. For the same reason, the height of the tip portion is relatively small compared to the diameter of the magnet. Typically, the ratio of the height of the tip portion to the diameter of the magnet is 1:1–1:2, such as about 1:1.5.

In the so-called micro-titration plate, where the wells are placed at 9 mm intervals, the dimensioning of a usable well 1 and rod 3 could be the following: inner diameter of the well 7 mm, outer diameter of the rod 4 mm, inner depth of the well (without the bottom recess 5) 10 mm, depth of the bottom recess and height of the rod tip portion 1.5 mm, width of the flat bottom 6 of the recess 1 mm, radius of curvature of the bottom corner of the wall about 1 mm, radius of curvature of the bottom recess wall about 5 mm, radius of concavity of the rod tip about 4 mm, height of the magnet 4 about 40 mm and diameter of the magnet about 3 mm. In view of the well of micro-titration plate, such a magnet actually is "overlong", however, this same rod can be used also in larger wells, e.g. with a height of about 25 mm, the volume being up to the order of 500 $\mu$l. A fairly long magnet also has the advantage of being easy to fasten to the support structures of the apparatus without requiring an intermediate adapter.

The bottom recess 2 and the rod tip portion ensure that the interstice between the wall of the well 1 and the rod 3 is large enough and that the rod can be inserted all the way to the recess bottom, despite positioning tolerances caused by the transverse motion.

The rod 3 can also be used in a conventional well with a flat or concave bottom.

The vertical movement also has specific tolerances, and as a result, the tip of the rod 3 does not necessarily always reach its lower position at the well bottom. With typical apparatus techniques, the maximum error caused by this is about ±0.5 mm. The relative inclination of the rod and the well causes an additional error. The error caused by this may be typically about ±0.3 mm. The relative inclination of a plate comprising several wells and a matrix comprising several rods causes an additional error. However, this error is small compared to those mentioned above.

The vessel and the rod can be made of suitable plastic, e.g. polypropylene.

The apparatus may be provided with vertical spring means to compensate for vertical motion tolerances.

The arrangement in FIG. 3 uses a plate 7, which comprises a plurality of rows of wells 1. Similarly, a number of rods equal to the number of wells in a row have been connected to an arm parallel to the row to form a jointly moved row of rods. Each rod 3 holds a magnet 4 fastened to the arm 8. At its upper end, the arm has a gripping means 9, with which the arm is vertically moved. The plate is placed on a base 10. The base yields in the vertical direction owing to vertical spring means 11. When the row of rods is introduced into the wells, it is driven against the bottom 6 of the bottom recesses 2 and even somewhat further. Then the springs will balance the distance between the tip and the bottom of each rod to a minimum (almost to zero in the practice).

Instead of the base 10, the fastening arm of the rods 4 can be provided with springs.

In addition or as an alternative, each arm 8 may be provided with springs separately. For this purpose, the gripping means 9 is placed glidingly between an upper stop 12 and a lower stop 13 in the arm, and between the gripping means and the lower stop, there is a spring 14 which presses the gripping means upwards.

The spring arrangement is especially useful when very small wells (e.g. 5 to 10 μl) are used. It is also particularly useful when large plates or plates comprising numerous wells are used.

What is claimed is:

1. A vessel and a rod to be used with the vessel for collecting magnetic particles from a liquid containing the particles in the vessel, or for releasing the particles into a liquid in the vessel, the rod being inserted into the vessel and removed from the vessel after the collecting or releasing operation, the vessel having an inner wall surface and a bottom wall surface, the bottom wall surface defining a depressed recess for receiving a tip end portion of the rod, the bottom wall surface comprising an annular surface region extending radially inwardly between the inner wall surface and a horizontal bottom surface region in the depressed recess, the annular surface region comprising a convex inflection surface region defining a circumferential rim to the depressed recess, the inner wall surface and the bottom wall surface together defining a vessel volume, wherein, a minimum distance maintained from the rod introduced into the vessel volume to the inner wall surface of the vessel is great enough at each point to prevent any liquid ring or ring part to be formed between the inner surface of the vessel and the rod, which ring would be removed along with the rod as the rod is lifted from the vessel.

2. A vessel and a rod as defined in claim 1, in which the minimum distance of the rod from the inner wall surface of the vessel at each point is at least about 1 mm.

3. A vessel and rod as defined in claim 2, in which the minimum distance of the rod from the inner wall surface of the vessel at each point is less about 1.5 mm.

4. A vessel and a rod as defined in claim 1, in which the horizontal bottom surface region has a diameter equaling combined positioning tolerances for any horizontal movements of the vessel and the rod.

5. A vessel and a rod as defined in claim 4, in which the horizontal bottom surface region has a diameter in the range of 0.5 mm to 2 mm.

6. A vessel and rod as defined in claim 5, in which the horizontal bottom surface region has a diameter of about 1 mm.

7. A vessel and a rod as defined in claim 1, in which the rod has a tapered tip end portion and in which the shape of the recess matches the shape of the tip end portion.

8. A vessel and rod as defined in claim 1, in which the bottom wall surface has a shape to direct liquid into the depressed recess.

9. A vessel and rod as defined in claim 1, in which the depressed recess is shaped to minimize free surface of liquid therein.

10. A vessel and rod as defined in claim 1, in which a surface of intersection between the inner wall surface and the bottom wall surface has a mildly concave curved shape.

11. A vessel and rod as defined in claim 10, in which the mildly concave curved shape has a radius of 0.5 mm to 2.0 mm.

12. A vessel and rod as defined in claim 11, in which the mildly concave curved shape has a radius of 1.0 mm.

13. A vessel and rod as defined in claim 1, in which the bottom wall surface slopes continuously from intersection with the inner wall surface to the depressed recess.

14. A vessel and rod as defined in claim 1, in which an interstice formed between a tip end portion of the rod engaged in the depressed recess and an opposed surface of the depressed recess is at most between 0.05 mm and 0.3 mm.

15. A vessel and rod as defined in claim 14, in which the interstice is at most between 0.1 mm and 0.2 mm.

16. A vessel and rod as defined in claim 1, further comprising means that yield in a direction of vertical motion of the rod as the rod is engaged against an inner bottom wall surface of the vessel.

17. A vessel and rod as defined in claim 16, in which the means that yield are provided in a base supporting the vessel.

18. A vessel and rod as defined in claim 16, in which the means that yield are provided in association with the rod.

19. A vessel and rod as defined in claim 16, in which the means that yield are provided in association with actuating gear for the rod.

20. A vessel and rod as defined in claim 16, in which the means that yield are provided in association with a plate supporting multiple vessels.

21. A vessel and rod as defined in claim, 16, 17, 18, 19, or 20, in which the means that yield comprise a spring.

22. A vessel and a rod to be used with the vessel for collecting magnetic particles from a liquid containing the particles in the vessel, or for releasing the particles into a liquid in the vessel, the rod being inserted into the vessel and removed from the vessel after the collecting or releasing operation, the vessel having an inner wall surface and a bottom wall surface and the rod comprising a tip end portion, the bottom wall surface comprising a depressed positioning recess into which the tip end portion is fitted for positioning the rod, the depressed positioning recess comprising a horizontal bottom surface region, the bottom wall surface comprising an annular surface region extending radially inwardly between the inner wall surface and the horizontal bottom surface region of the depressed positioning recess.

23. An apparatus for collecting magnetic particles from a liquid containing the particles in a vessel or for releasing the particles into a liquid in the vessel by means of a rod, the rod being inserted into the vessel and removed from the vessel after the collecting or releasing operation, the apparatus comprising means that yield in a direction of vertical motion of the rod as the rod is engaged against an inner bottom wall surface of the vessel.

24. A vessel and rod as defined in claim 23, in which the means that yield are provided in a base supporting the vessel.

25. A vessel and rod as defined in claim 23, in which the means that yield are provided in association with the rod.

26. A vessel and rod as defined in claim 23, in which the means that yield are provided in association with actuating gear for the rod.

27. A vessel and rod as defined in claim 23, in which the means that yield are provided in association with a plate supporting multiple vessels.

28. A vessel and rod as defined in claim 23, 24, 25, 26, or 27, in which the means that yield comprises a spring.

* * * * *